United States Patent [19]

Costin

[11] Patent Number: 5,520,633
[45] Date of Patent: May 28, 1996

[54] COMPUTER CONTROLLED SMART PHACOEMULSIFICATION METHOD AND APPARATUS

[76] Inventor: John A. Costin, 6841 Cliffside Dr., Vermilion, Ohio 44089

[21] Appl. No.: 148,315

[22] Filed: Nov. 8, 1993

Related U.S. Application Data

[63] Continuation of Ser. No. 810,428, Dec. 20, 1991, Pat. No. 5,279,547, which is a continuation-in-part of Ser. No. 635,887, Jan. 3, 1991, Pat. No. 5,610,317.

[51] Int. Cl.$^6$ .................................................. A61B 17/20
[52] U.S. Cl. .............................. 604/22; 601/2; 606/169; 606/170; 606/171
[58] Field of Search ................................ 604/22; 601/2; 606/159, 169–171

[56] References Cited

U.S. PATENT DOCUMENTS

| | | |
|---|---|---|
| 3,601,126 | 8/1971 | Estes et al. . |
| 3,812,855 | 5/1974 | Banko ........................... 128/24 AA |
| 3,812,858 | 5/1974 | Oringer . |
| 3,902,495 | 9/1975 | Weiss et al. ............................ 604/22 |
| 3,930,505 | 1/1976 | Wallach . |
| 3,964,487 | 6/1976 | Judson . |
| 4,024,467 | 5/1977 | Andrews et al. . |
| 4,024,866 | 5/1977 | Wallach . |
| 4,114,623 | 9/1978 | Meinke et al. . |
| 4,126,137 | 11/1978 | Archibald . |
| 4,168,707 | 9/1979 | Douvas et al. ........................ 604/107 |
| 4,184,510 | 1/1980 | Murry et al. .......................... 604/22 |
| 4,223,676 | 9/1980 | Wuchinich et al. . |
| 4,496,342 | 1/1985 | Banko . |
| 4,508,532 | 4/1985 | Drews et al. ........................... 604/22 |
| 4,590,935 | 5/1986 | Ranalli .................................... 604/22 |
| 4,651,280 | 3/1987 | Chang et al. . |
| 4,658,819 | 4/1987 | Harris et al. . |
| 4,705,500 | 11/1987 | Reimels et al. ......................... 604/22 |
| 4,712,544 | 12/1987 | Ensslin . |
| 4,739,759 | 4/1988 | Rexroth et al. . |
| 4,750,488 | 6/1988 | Wuchinich et al. . |
| 4,770,654 | 9/1988 | Rogers et al. . |
| 4,793,346 | 12/1988 | Lehmer . |
| 4,969,885 | 11/1990 | Farin . |
| 4,989,588 | 2/1991 | Kubota et al. . |
| 5,026,387 | 6/1991 | Thomas .................................. 604/22 |
| 5,139,509 | 8/1992 | Fischer et al. . |
| 5,151,085 | 9/1992 | Sakurai et al. ......................... 604/22 |
| 5,180,363 | 1/1993 | Idemoto et al. ........................ 606/45 |
| 5,279,547 | 1/1994 | Costin .................................... 604/22 |

FOREIGN PATENT DOCUMENTS

| | | |
|---|---|---|
| 359217 | 3/1990 | European Pat. Off. . |
| 8705793 | 10/1987 | WIPO .................................... 604/22 |

*Primary Examiner*—Corrine M. Maglione
*Assistant Examiner*—N. Kent Gring
*Attorney, Agent, or Firm*—Fish & Richardson

[57] ABSTRACT

A method and apparatus for operating on the human eye detects changes in load, more specifically, mechanical impedance, of the transducer and controls aspiration based on the load changes. A change from a lower load to a higher load indicates that harder tissue is being encountered and accordingly causes aspiration amount to increase. Conversely, a change from a higher load to a lower load indicates that aspiration amount should be quickly decreased since the tissue which is being encountered is softer. One way to detect the impedance is by a sensor, e.g., a piezoelectric element coupled to the operating needle detecting the movement thereof.

29 Claims, 11 Drawing Sheets

COMPUTER CONTROLLED SMART PHACOEMULSIFICATION METHOD AND APPARATUS

This is a continuation of application Ser. No. 07/810,428, filed Dec. 20, 1991, allowed Jun. 16, 1993 U.S. Pat. No. 5,279,547; which is a continuation-in-part of application Ser. No. 07/635,887 filed Jan. 3, 1991, U.S. Pat. No. 5,160,317.

FIELD OF THE INVENTION

The present invention relates to a computer controlled "smart" phacoemulsification apparatus, and more specifically to one which controls power delivery to the needle of the transducer and also controls an amount of aspiration based on a load on the tip of the transducer.

BACKGROUND AND SUMMARY OF THE INVENTION

Eye surgery is a complicated and delicate process. One common eye surgery is cataract extraction. There are currently several methods of acceptable cataract extraction, including phacoemulsification. Phacoemulsification is not in itself new, but as currently done has many problems.

Phacoemulsification involves the generation of an ultrasonic signal which is a series of cyclical mechanical vibrations in a frequency range beyond that detectable by normal human hearing. The ultrasonic signal is generated by a transducer that is driven by an electrical signal in a frequency range between 20 and 100 kilohertz in equipment presently available for this application. Typically the transducer mechanism includes either piezoelectric or magnetostrictive elements.

The energy resulting from the ultrasonic signal is coupled to the human lens by a needle attached to the transducer. Typically the needle is made from an inert alloy of titanium or stainless steel. Once coupled to the human lens, the ultrasonic energy fragments and emulsified the cataract. Once this nuclear material is fragmented, however, it must be removed from the eye. In order to do this, the ultrasonic needle is hollow, and an aspiration system is connected to the hollow area in order to remove the fragmented particles. A balanced salt solution is also injected in order to maintain the stability or pressure, and this infusion occurs around the vibrating titanium needle through a sleeve.

An example of such a phacoemulsification unit is shown in U.S. Pat. No. 4,223,676, the disclosure of which is hereby incorporated by reference. Current phacoemulsification surgery allows the surgeon to choose either a fixed phaco mode in which the power setting to the transducer is fixed, or a linear mode in which the phaco power can be changed by the power peddle. In the fixed mode, the phaco unit is either on or off depending on whether the peddle is depressed or not. The value of power setting is preset. In the linear mode, the further depression of the peddle varies the amount of power to the transducer and thereby the ultrasonic energy. The aspiration during this operation is preset. A third mode of phacoemulsification which has been recently introduced keeps the phaco power fixed and varies the aspiration depending on the foot peddle.

Figure 1:
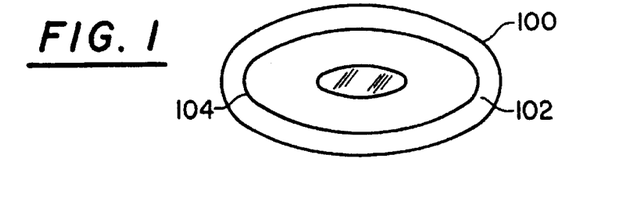
FIG. 1 shows a schematic view of the human eye.
Figure 2:
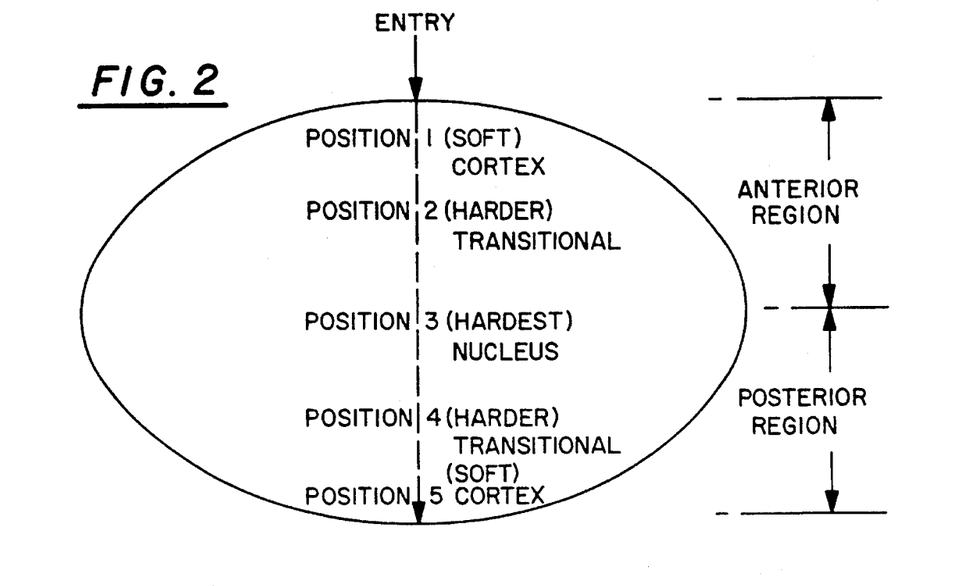
FIG. 2 shows a representative amount of aspiration required in a traversal through the eye.
Figure 2A:
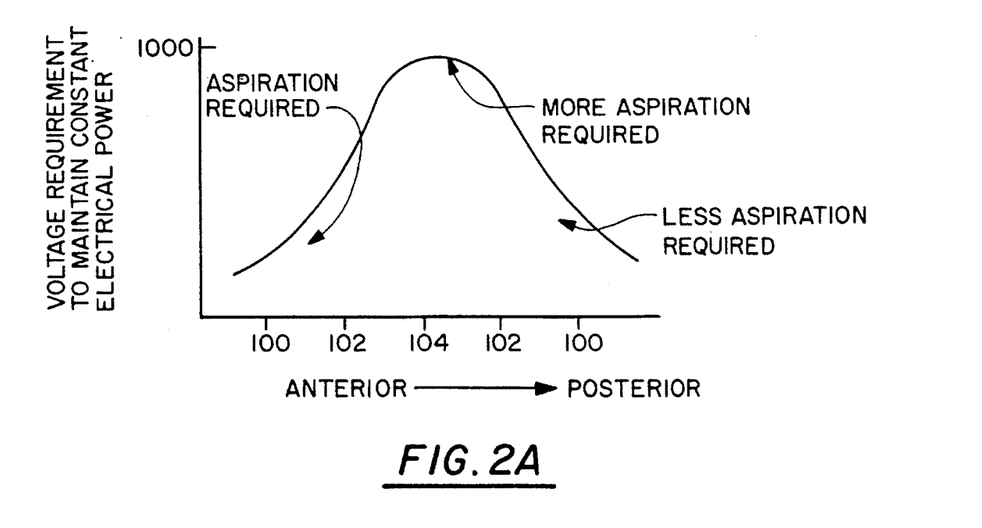

The inventor of the present invention has recognized a problem which exists in these prior operations. In order to fully understand this, one must consider the structure of the lens of the human eye. FIG. 1 shows diagrammatically a human lens which has an outer, fine, transparent tissue or capsule shown as layer 100. Anterior to this is a soft material known as the cortex 102, which surrounds the transition layers 104. The nucleus of the lens is a hard, compressed lens material shown as 106. The inventor of the present invention has first noted that in these soft outer cortical layers, little aspiration is required, but more aspiration is required in the harder transitional layers and even more in the hardest nucleus layer. However, posterior to the hardest nucleus layer is a less hard transitional layer followed by a soft cortex. A majority of the complications during eye surgery are caused not by the amount of phacoemulsification, but by overaspiration in conjunction with the emulsification causing a "punch through" through the posterior lens capsule. This is particularly dangerous since the center of the lens needs more energy (aspiriation and emulsification) than the outer soft cortical layer, and therefore there is more possibility of punch-through at this higher energy level and high aspiration level.

Eye surgery involves forming an opening in the front of the capsule, and locating the phaco needle first into the soft cortex. At this time the needle will experience a minimal load in the soft cortex. As the needle goes further into the nucleus which is progressively harder, the mechanical load increases. After passing through the nucleus, the process reverses, and the mechanical load will quickly decrease. It is at this point that the inventor of the present invention has found that the control of aspiration becomes critical. Overaspiration at this time can cause the posterior capsule to be ruptured. However, determination of the relative hardness of these layers has previously been left to the observation skills and manual skills of the surgeon. However, the surgeon has many other things on his mind and also simply may not be able to react fast enough in order to properly change the aspiration amount.

The inventor of the present invention has recognized that a hard nucleus consumes more energy than a soft nucleus, thereby changing the impedance, and more specifically the mechanical impedance, introduced to the ultrasonic tip. According to the present invention, this difference is fed back to a microprocessor in order to modify the aspiration system dependent on the hardness of the material being operated upon. This reduces the problem of "punch through" because it allows automatic checking of the hardness of the material and automatic adjustment of the aspiration delivery in a way which is faster than could ever be done using human reflexes. Such a system has never been described in the prior art. One way in which this is done is by detecting mechanical impedance of the tissue, using, for example, a sensor to detect response to a stimulus.

One general feature of the present invention is the recognition by the inventor of the present invention that soft tissue requires a low stroke or low velocity and that hard tissue requires a high stroke and high velocity. The mechanical impedance of any material including the human eye is a function of the density $\rho$ and sound velocity C. It usually has a resistive component $R_C$ and a reactive component $X_L$. Compliant or deformable tissue presents primarily a resistive impedance to the driving force. Non-compliant or non-deformable tissues are primarily a reactive impedance. In other words, soft tissue will be more resistive and hard tissue will be more reactive.

Figure 14:
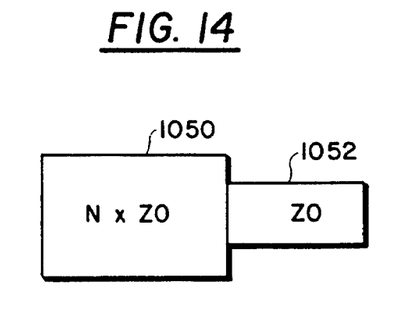
FIG. 14 shows a typical phaco needle.

One approach to detecting mechanical impedance from a piezoelectric hand piece is to read the driving voltage and current. Here not only magnitude but also phase will be monitored where zero phase difference will indicate a resistive load on soft tissue. A large phase difference would indicate a reactive load or hard tissue. Another approach would include determining the resonant frequency of the loaded hand piece in relation to a reference, which can be the resonant frequency of the unloaded hand piece. If the transducer is formed as a half wavelength straight bar, its resonant frequency will not change for purely resistive loads and can be determined according to the equation $$\tan\left(\frac{2\pi f}{c} x\right) = 0$$

where f is the operational frequency, c is the speed of sound in the bar, and x is the length of the bar. For a purely reactive load, the resonant frequency is determined by the equation $$\tan\left(\frac{2\pi f}{c} x\right) = \frac{X_L}{Z_0}$$

where XL is the reactive load and Z0 is the characteristic impedance of the bar. If the transducer is made as a step horn type to provide amplification of the displacement, the resonant frequency will change for either resistive or reactive loads. A typical step horn device is shown in FIG. 14 with its two parts 1050 and 1052. The lengths X of the parts 1050 and 1052 are equal to one another but their areas differ by a factor of N>10.

For a device of this type, the resonant frequency is determined according to the equation $$\tan\left(\frac{2\pi f}{c} x\right) = \frac{R_L}{Z0}$$

where X is the length shown in FIG. 14 and Z0 is the characteristic impedance of the transducer material as shown in FIG. 15. The part 1052 has the impedance Z0 while the part 1050 has the characteristic impedance N×Z0. For purely reactive loads the resonant frequency can be determined from the equation $$\left(\tan \frac{2\pi f}{c} x\right) = \left(\frac{X_L}{Z}\right)^2.$$

These equations are general and exemplary and different needle/transducer arrangements could use different equations.

Many attempts have been made in the prior art in order to attempt to automate operation processes. U.S. Pat. No. 4,223,676 is one such attempt and defines one type of ultrasonic aspirator of the type previously described above. Column 8 of this patent recognizes that frequency fluctuates during the course of an operation, and in order to attempt to maintain the amount of power delivery as constant, this patent teaches monitoring actual and expected parameters of the system. The difference between these two parameters is fed back in a feedback loop to control the stroke level of the vibrator. Therefore, while the power of the system is controlled, there is no teaching of controlling the amount of aspiration, and as such the problem of "punch through" would still remain in this system.

Similarly, U.S. Pat. No. 3,964,487 teaches a structure which monitors the impedance of the electric cutting apparatus, and feeds back this impedance to determine the amount of power to be provided. This device does not teach controlling the amount of aspiration, and therefore would not alleviate the problem of "punch through".

Similarly, U.S. Pat. No. 4,126,137 teaches sensing of the impedance of the tissues to set the amount of drive to an electro-surgical unit.

U.S. Pat. No. 4,024,866 relates to a device which teaches controlling the amount of suction in a suction conduit for eye surgery. Column 7, lines 24 ++ teach that an upper limit is placed on the amount of suction to prevent an excessive amount of suction. While this might provide an upper limit, it does not help the user to obtain better control and better feedback within the system

BRIEF DESCRIPTION OF THE DRAWINGS:

These and other aspects of the invention will now be described in detail with reference to the accompanying drawings, in which.

Figure 3:
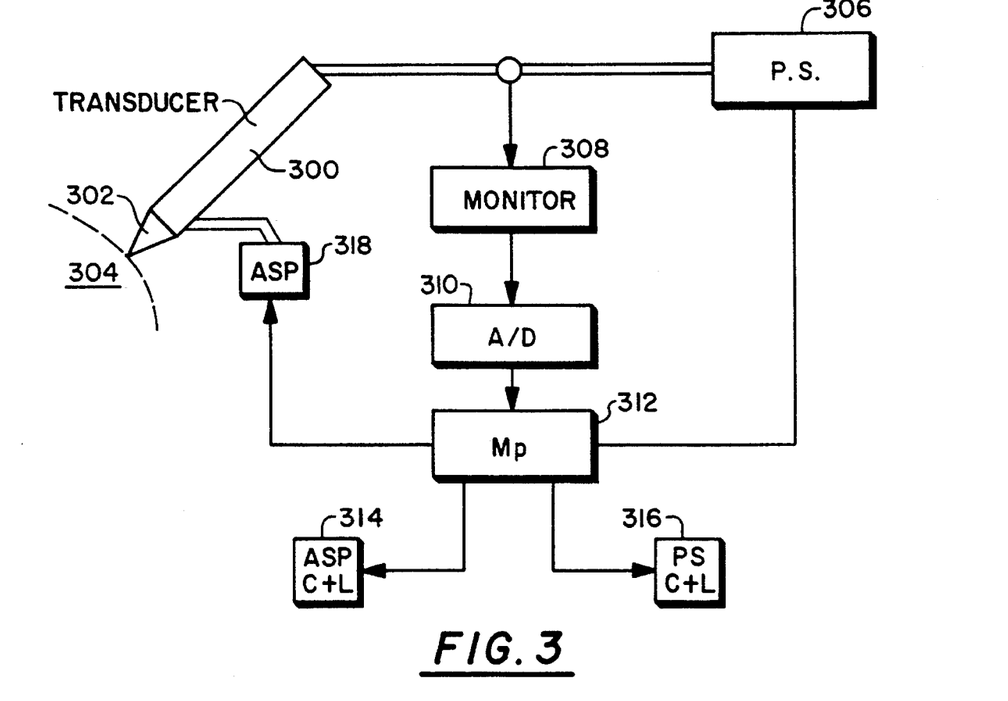
FIG. 3 shows a block diagram representation of a first embodiment of the present invention.

DESCRIPTION OF THE PREFERRED EMBODIMENTS:

A presently preferred embodiment will now be described in detail with respect to the accompanying drawings. FIG. 3 shows a first embodiment of the invention. Transducer 300 is shown attached to phaco needle 302 which is adapted to come into contact with a lens 304 of the human eye. The power supplied by power supply 306 to the transducer 300, and at the same time the voltage and current is monitored by monitor 308. Monitor 308 monitors the voltage and current, and produces analog signals which are converted by analog to digital converter into digital signals, and are input to microprocessor 312. Microprocessor 312 can be any commercially available type. An aspiration control 314 is also input to microprocessor as is a power supply control 316. These devices can be either dial-type potentiometers or the usual surgeon's foot peddle, and produce a command signal indicative of the amount of aspiration and power respectively desired. Microprocessor 312 produces analog signals which control the aspiration unit 318 in the power supply 306.

Figure 4:
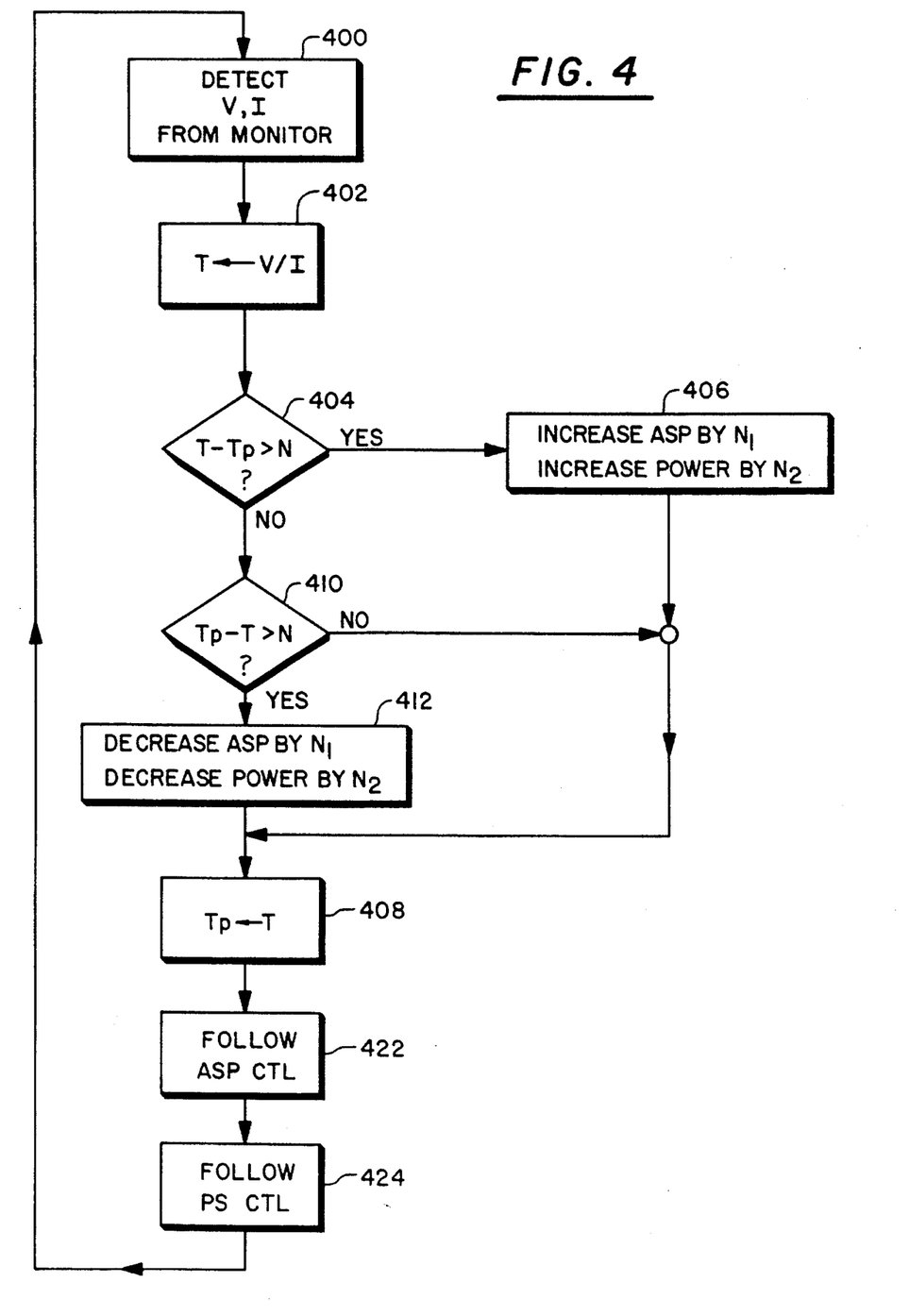
FIG. 4 shows a flow chart of operation of this first embodiment.

The microprocessor operates according the flowchart of FIG. 4, and accordingly controls the aspiration 318 and power supply 306 based on this flowchart. Step 400 detects voltage and current from monitor 308, and takes a ratio between this voltage and current at step 402. This ratio is stored in a variable T. This variable measures a linkage of the instantaneous aspiration with varying phaco needle load and can be implemented in at least two different forms.

First we must recognize that a positive correlation has been established between the electrical power consumed by an ultrasonic transducer and the mechanical motion of a needle attacked to it. One way, therefore, would be tracking impedance (voltage in/current in).

$$\text{impedance} = \text{voltage} \times \frac{1}{\text{current}}$$

$$Z = V \times \frac{1}{I}$$

A multiplier circuit could be used to accomplish this. Changes in the load would allow the control system to compensate in a variety of ways by affecting both electrical power and aspiration levels. Alternately, the difference between commanded power levels and actual power consumed could also be measured directly with only one multiplier circuit i.e.

power=voltage×current p=V×I

Both power levels (V*I) and V/I are referred to generically herein as "Impedance".

Step 404 makes a test by taking the current variable T and subtracting a previous value of the variable T called herein $T_P$, and then determining if $T-T_P$, is greater than a value N. If it is, this means that the impedance of the tissue currently is greater than the impedance at a previous time and that the current tissue is therefore harder than the previous tissue. Therefore, if the test at step 404 is positive, step 406 is executed which increases the aspiration rate by $N_1$ and increases the power by $N_2$. The flow then passes to step 408 in which the current value of T is stored in the location $T_P$ in preparation for a following cycle.

If the result at step 404 is negative and the difference between T and $T_P$ is not greater than N, a second test is made at step 410. Step 410 determines if the value of T, is greater than the current T by the amount N. If not, flow again passes to step 408. Therefore, if the difference between T and $T_P$ is less than the value N, no modification of aspiration or power takes place.

If $T_P$ is greater than T by more than the amount N, this indicates that the impedance at the previous time is greater than the impedance at the current time. Accordingly, the aspiration is decreased by the value $N_1$ and the power is decreased by the value $N_2$ at step 412.

The following steps, 420 and 422, follow the lead of the aspiration controller 314 and power supply controller 316 respectively. If these values are increased, the power to the appropriate component i also increased, according to a previously designated algorithm.

The specific structure and method steps enabling control of both power and aspiration according to the impedance encountered by the transducer is in no way taught or suggested by the prior art and is totally novel thereover.

Figure 5:
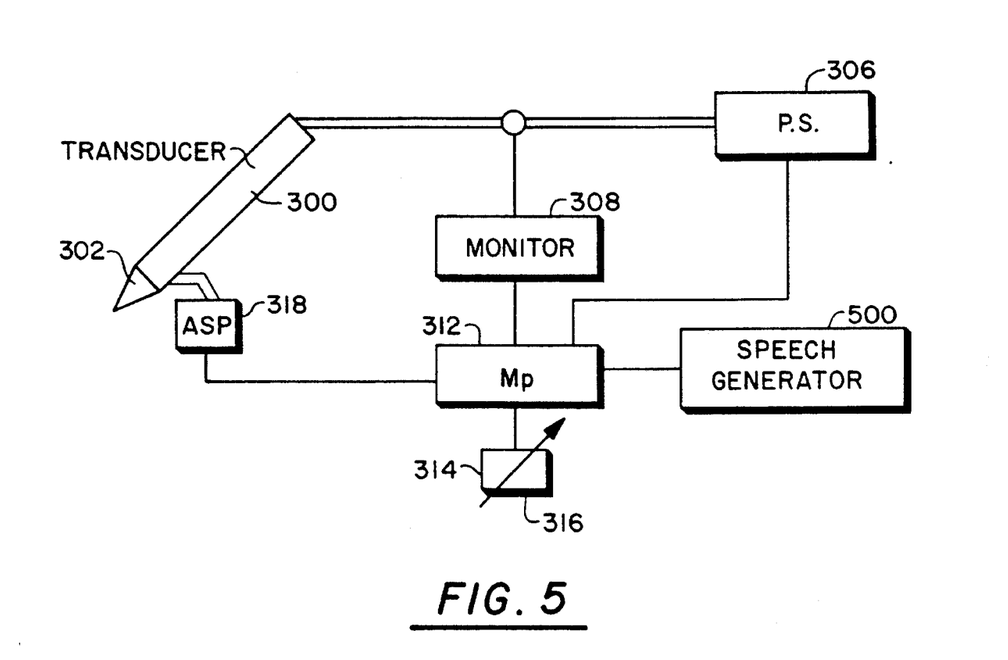
FIG. 5 shows a block diagram representation of a second embodiment of the present invention which uses a speech enunciator to aid the surgeon with his operation.

A second embodiment of the invention is shown in FIG. 5 where like numerals represent like elements. This second embodiment of the invention uses, in addition to the above monitoring system, a speech generating module 500 which enables talking to the surgeon while he is operating.

Current phaco units have visual displays and audio feedback. The visual displays may show the mode in which the machine is engaged, for instance, foot peddle position and irrigation only, irrigation and aspiration, etc. The audio feedback may be different sounds in different units that indicate a transition, such as a beep or click.

However, all of these sounds may be very confusing to a surgeon who is first learning to do the phaco procedure. Such a surgeon has many other things to concentrate on and often times finds extra confusion in where on the foot peddle they are and precisely what is happening. The second embodiment of the present invention enables the use of commercially available speech generating equipment to help avoid this confusion.

Figure 6:
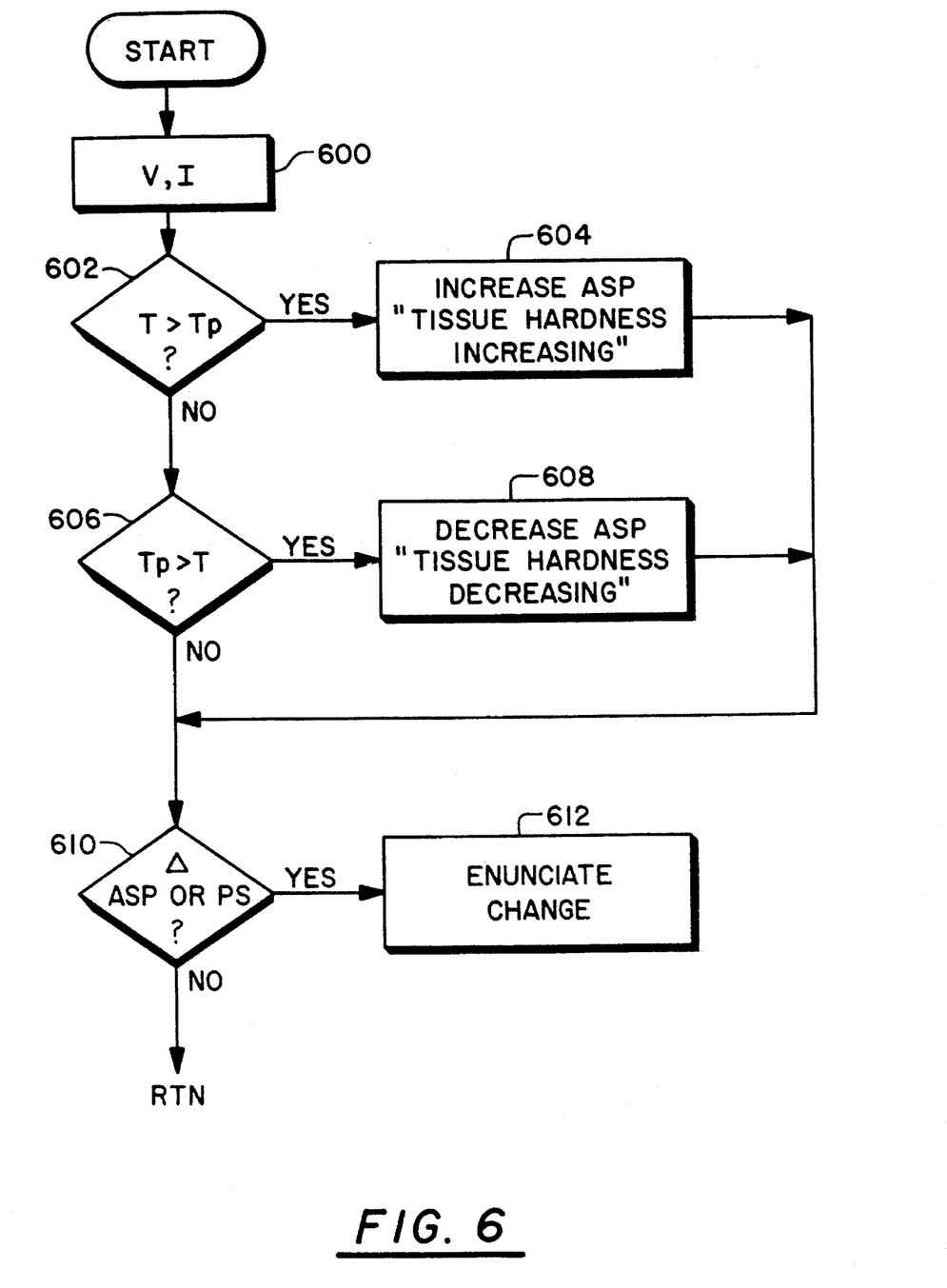
FIG. 6 shows a flow chart of operation of the second embodiment.

According to this embodiment of this invention, the speech generating unit 500 can be a commercially available speech generating chip and audio equipment, or it can be, for instance, a series of tapes or recorded tracks which can be accessed by an appropriate processor. Such devices are well known in the art and will not be discussed further. This device operates according to the flowchart of FIG. 6. FIG. 6 has many common elements with FIG. 4, and starts out in step 600 with detecting V and I and the value T. Step 602 determines if T is greater than $T_P$ by the value N, and if so, increases aspiration and power and also energizes speech generator 500 to say "tissue hardness increasing". Step 606 determines if $T_P$ is greater than T by a certain amount, and if yes, executes steps 608 by decreasing aspiration and enunciating that the tissue hardness is decreasing. Step 610 determines if there has been a change in aspiration or power supply control and if so, enunciates this change. For instance, a foot peddle in position one might be enunciated to say "irrigation" and in position 2 would be enunciated as "irrigation and aspiration". The enunciator might also say "phaco fixed at 10%" or "phaco increased to 15%" and as the foot peddle or similar device was altered, then the enunciator could express, in increments, the new values.

This would enable the surgeon to maintain his concentration during this very difficult time of the operation.

Figure 7:
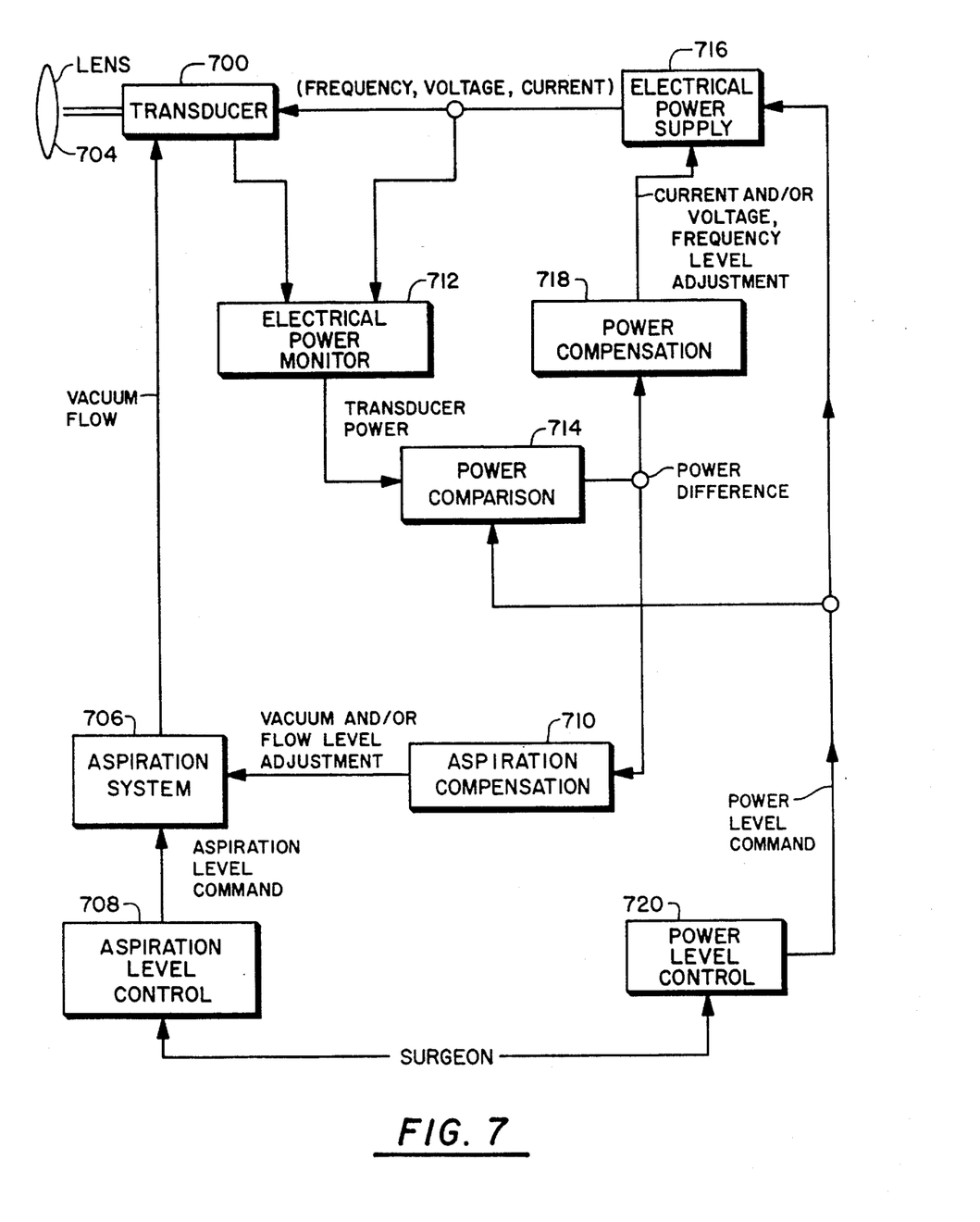
FIG. 7 shows a structure of the third embodiment of the present invention.

A third embodiment for the smart phacoemulsification system is described with reference to FIG. 7 and the flowchart in FIG. 8. The key to the successful operation of this system is twofold. First, the surgeon has independent control over both transducer load power and aspiration reference levels. Secondly, the automatic control system power monitor and both power and aspiration compensation mechanisms provide measured improvements in the surgeon's control of the transducer by linking the aspiration system compensation with the drive signal for the power compensation.

Electrical power supply 716 provides voltage and current at some frequency to transducer 700. Needle 702 makes contact with the human lens 704 and experiences a varying mechanical load dependent on the density of tissue layers. The surgeon establishes reference power and aspiration levels via power level control 700 and 708 aspiration level control 708. Electrical power supply 716 responds to power level commands and to power compensation commands (voltage, current or possibly frequency adjustments). These commands originate from modules 720 and 718 respectively. The varying mechanical load on needle 702 is reflected via transducer 700 as a changing electrical load consuming different amounts of electrical power from the reference power level command. This parameter detection is referred to herein as mechanical impedance.

Power monitor 712 senses load voltage and current from transducer 700 and computes electrical power. Transducer power consumption is fed to power comparison module 714 which outputs a difference between actual transducer power and the independent reference level from the power command. Power compensation module 718 responds by appropriate electrical adjustments to power supply 716 such that transducer power consumption will track the independent command from the surgeon.

The unique safety improvement feature of this system results from the application of the power compensation drive signal (power comparison output) to the aspiration compensation module 710. The output of the aspiration compensation module 710 will be an adjustment to vacuum, or flow or both, depending on the type of aspiration system.

As with power the surgeon has independent input control via aspiration control 708 to press the output (vacuum and flow) of aspiration system 706. The entire system follows a straightforward control scheme as described by the flowchart of FIG. 8. note that any changes induced by the compensation modules will force the load power to track the independent power level command from the surgeon. Also, the aspiration changes will be added to the independent aspiration level commands from the surgeon. In this way, the surgeon maintains control over the procedure.

Figure 8:
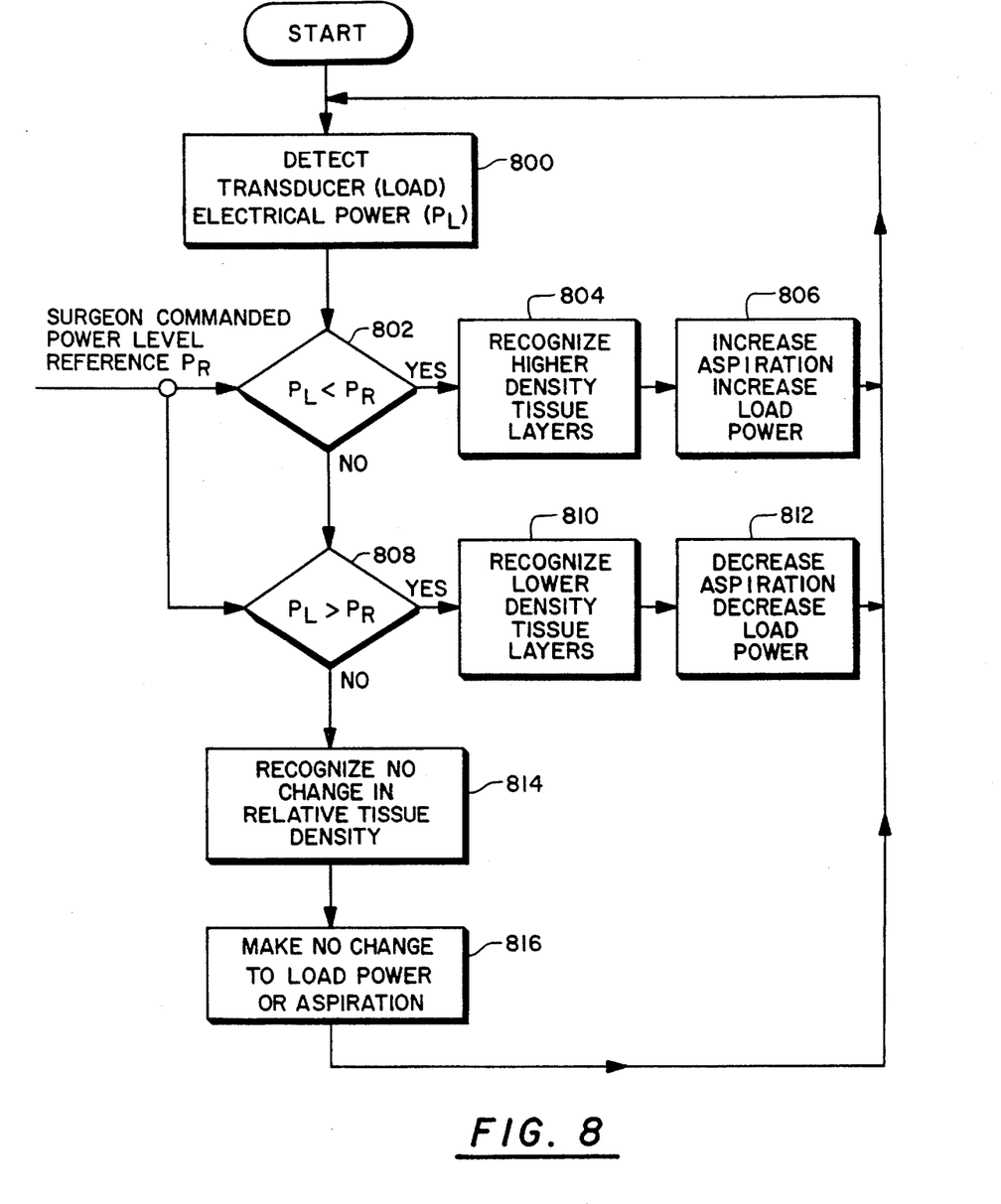
FIG. 8 shows a flow chart of this operation.

The FIG. 8 flowchart shows detecting the transducer load and electrical power at step 800, followed by determinations at step 802 and 808 as to whether the power is less than or greater than a reference $P_r$. If the current electrical power $P_1$ is less than $P_4$, higher density tissue layers are recognized at step 804, followed by the aspiration increase load power at step 806. If the load $P_1$ is recognized as greater than $P_r$ at step 808, lower density tissue layers are recognized at step 810, followed by a decrease in the aspiration and step 812. Step 814 determines if no change in relative tissue density is recognized, followed by no change in load power or aspiration at step 816.

Figure 9:
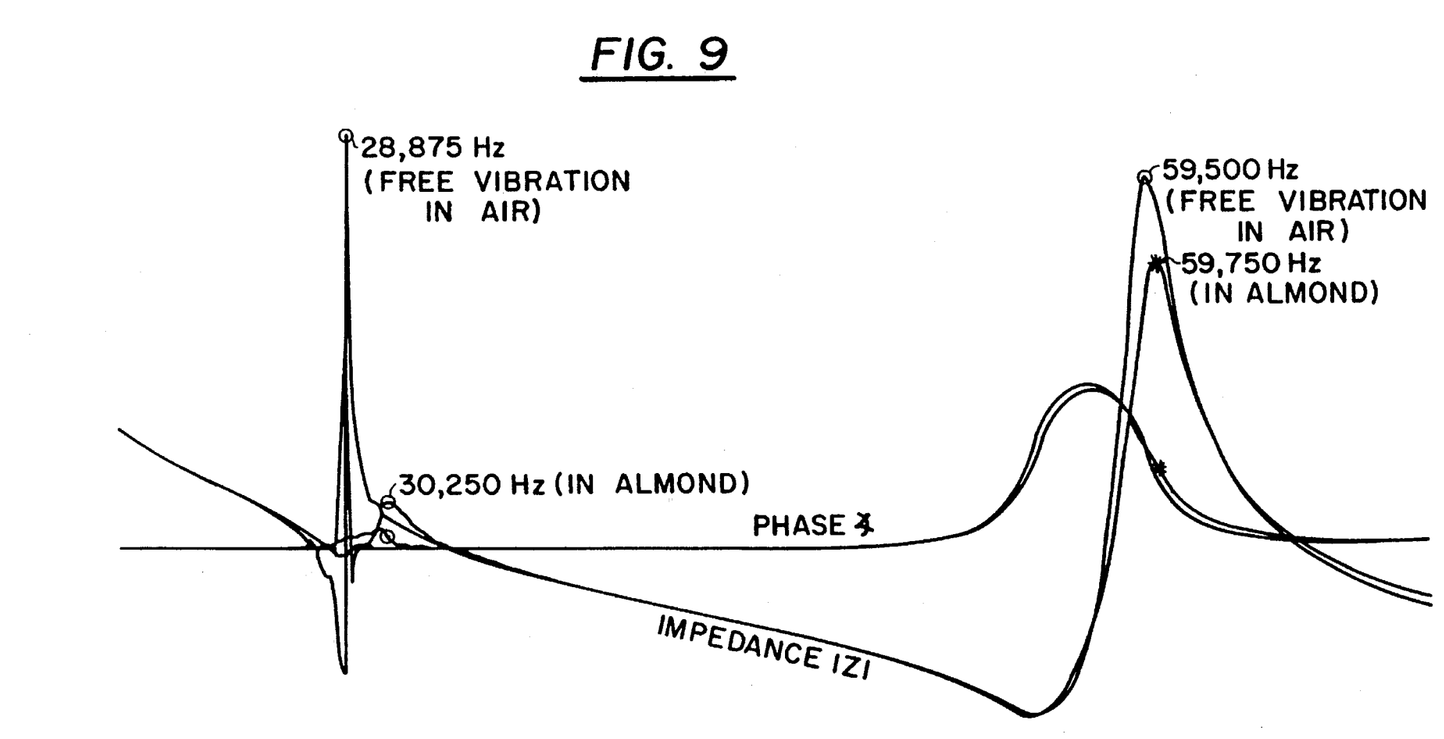
FIGS. 9 and 10 show characteristic curves for characteristics in Almond, and a peanut "M & M(TM)" respectively.

Experiments have been carried out to verify that both mechanical impedance and resonant frequency change is a function of the hardness of material that is encountered by phaco needle 302 during such operations. FIG. 9 shows an actual experimentally obtained mechanical impedance versus frequency spectra of loaded and unloaded phaco needles. This was measured with a Hewlett Packard impedance analyzer using ±2 volts excitation, and a hard almond, used in simulating a hardened lens portion of an eye. FIG. 9 shows the change in phase and impedance shifting with loading. Two resonant peaks were observed at approximately 28.875 KHZ and 59.5 KHZ. It is believed by the applicant that these two peaks correspond to the fundamental electromechanical resonance of the piezoelectric driving crystal. These two peaks may also be due to the longitudinal and transverse piezoelectric coefficients of the crystal.

Figure 10:
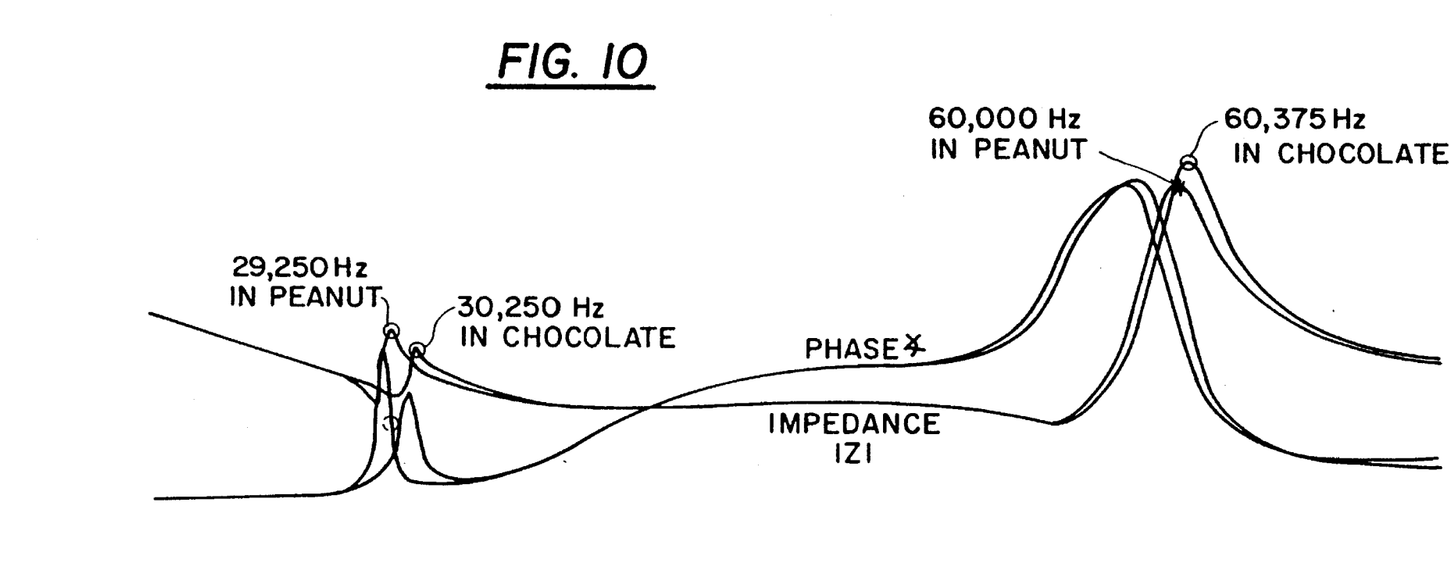

The second impedance spectrum shown in FIG. 10 shows the change in hardness effects as simulated by a chocolate covered peanut M&M (TM) candy. The frequency of shifts of the two resonant peaks are approximately one 1 KHZ and 375 hertz for the low and high frequency resonant peaks respectively. This demonstrates the practicability of the system by its ability to determine a peanut within a chocolate covered M&M peanut candy.

In operation, a map will be formed between the phase angle (resonant frequency), mechanical impedance, and hardness of the material. This map can be from a plot such as shown in FIGS. 9 and 10, made while observing the characteristics of the material on which the operation is occurring.

While these changes in impedance can be determined and the observation of the frequency shift can also be determined as the phaco needle encounters loads of different hardness, it has been found that it may be difficult to identify these changes under high level excitation (110 volt) conditions due to the high electrical noise. The impedance and frequency shift are more easily observable under low level excitation conditions of such as ±2 volts, but detection of this on a practical scale requires more specialized techniques than those of the previous embodiments.

Figure 11:
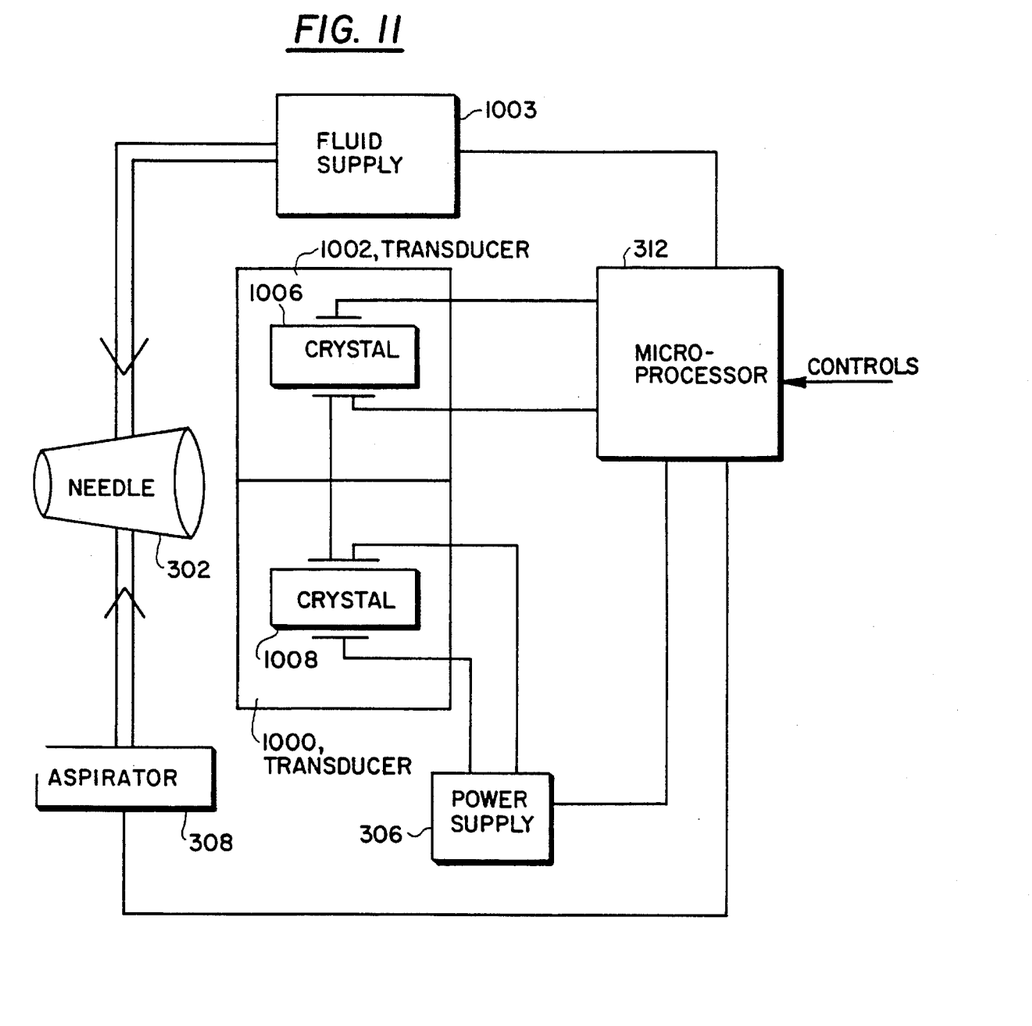
FIG. 11 shows a block diagram of a fourth embodiment of the invention.

In order to effect this low level process, the fourth embodiment of the present invention detects the change in hardness of the material by the addition of solid state microsensors which provide the means of load hardness detection without electrical interference from the large voltages driving the piezoelectric or magnetostrictive crystal. FIG. 11 shows a general block diagram of a structure using the process, it being understood that the concepts of all the previous embodiments could be added to the basic modification of FIG. 11.

FIG. 11 shows the improved structure for load sensing defined according to the fourth embodiment. This fourth embodiment includes two force transducers 1000 and 1002. The force transducer 1000 is a driving force transducer which is driven by power supply 306 under control of microprocessor 312. The voltage excitation to the first force transducer 1000 causes expansion and contraction of phaco needle 302. An aspirator 308 and fluid supply 1003 is also provided. It should be understood that FIG. 11 may also include the auxiliary structure shown in any of FIGS. 3–8, although this is not shown in detail for easier understanding.

The driven element 1002 includes a separate piezoelectric crystal 1006 which is stressed at the resonant frequency of the combined electrical and mechanical circuit and for this purpose is mechanically coupled to phaco needle 302. This mechanical coupling provides the second piezoelectric crystal mechanically in parallel with a first piezoelectric crystal 1008 of the first force transducer 1000 to sense the movement of the needle 302 in this way. Needle 302 is moved by a large surge of voltage which can cause noise in the resultant measurement. However, the auxiliary crystal 1006 is moved by the movement of the needle, rather than by the driving voltage. The compression and release gives off a voltage that is proportional to this amount of compression of the piezoelectric crystal in correspondence with known characteristics of the crystal. The microprocessor 312 therefore obtains a voltage related to the amount of contraction of the crystal, as well as a voltage indicative of the amount of power provided to the crystal 1000, this power being coupled to the needle 302 to drive it. This driven element 1002 has been called a "pony" element by the inventor, since it "rides" on the phaco needle.

The secondary sensing element 1002 is placed in a location to convert the mechanical stress thereon into electrical voltage or current. These elements can be placed at nodal points where the stress/velocity is maximum or antinotal points where the stress/velocity is minimum. The signals generated by the sensors will comply with the characteristic equations for the transducer when two sensing elements are used in a differential configuration to cancel errors.

In one approach, the impedance would be continually monitored as the transducer and in another approach the transducer would pulse with the first period of the pulse being used as a sensing period of time with the following period being used as a operating period. During the sensing period the power of the transducer is lowered to a level below which cavitation will not occur and transducer losses are minimum.

The amount of aspiration is then defined as a function of flow rate and vacuum level and either or both of these can be controlled.

Figure 12:
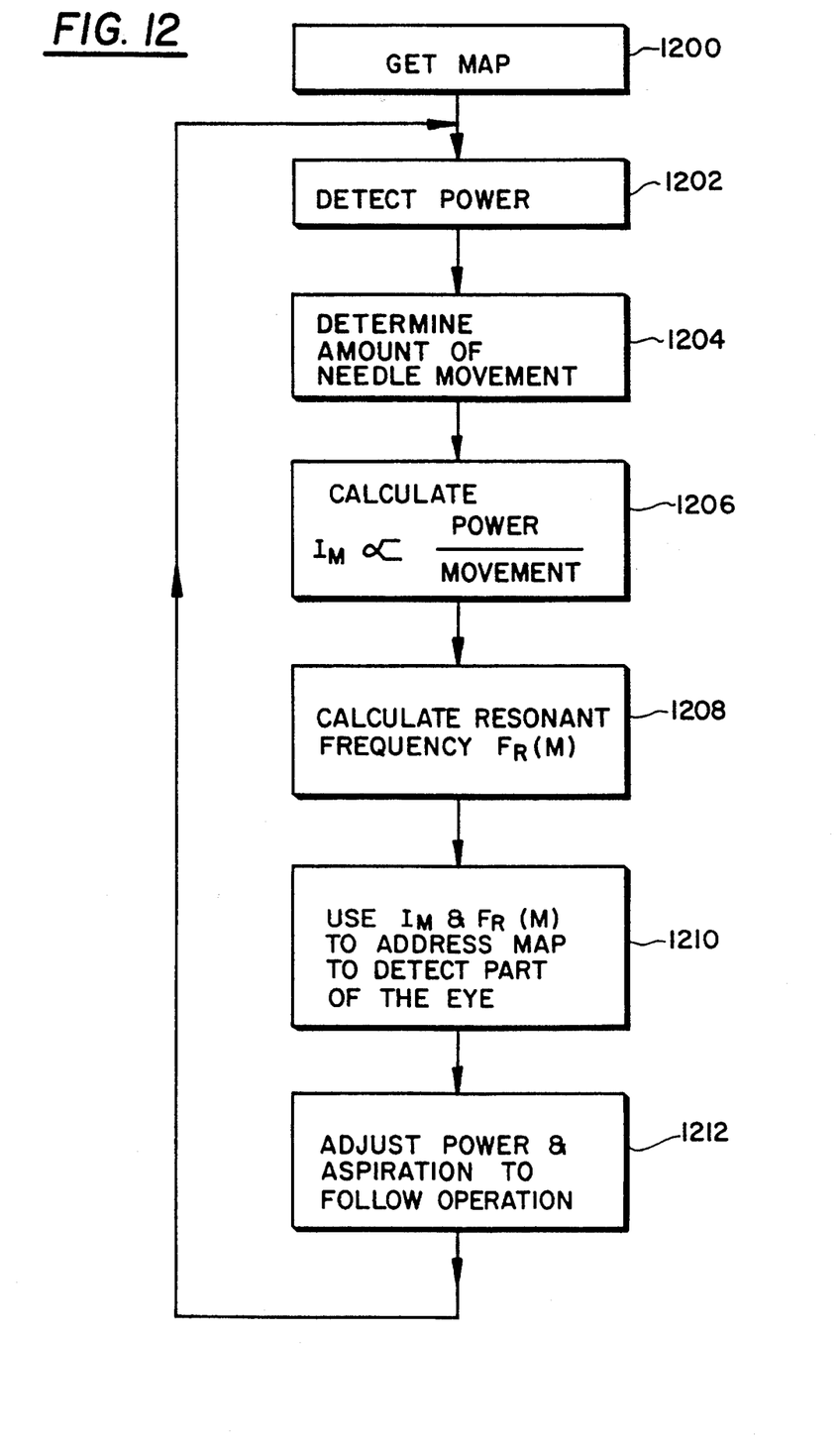
FIG. 12 shows a flowchart of operation of this fourth embodiment.

The operation of this structure takes place accordance with the flow chart of FIG. 12. The flow chart of FIG. 12 shows the operation of the present invention, it being understood that this operation might need to be modified somewhat. However, these modifications could easily be done by those of skill in the art by repeating the simulation discussed above with respect to FIGS. 9 and 10. While FIGS. 9 and 10 used an almond and a M&M respectively, actual values for cut-off could use an actual human eye from a cadaver or an animal for better simulating the exact characteristics that will need to be controlled.

FIG. 12 starts with step 1200 of getting a map. This map, however, must be determined and stored in advance, and would typically be done by making similar plots to those of FIGS. 9 and 10. While the simulations of FIGS. 9 and 10 were done with various commercially available food materials which had varying hardnesses, an actual map for the system would be better conducted using an actual human eye from a cadaver or the like. A similar simulation to that shown in FIGS. 9 and 10 is conducted on such an eye and a characteristic chart showing both the mechanical impedances of such a material as well as the resonant frequencies thereof should be stored as a one or two dimensional map. This map is the map that is obtained in step 1200.

The actual flow chart begins with step 1202 where the amount of the needle movement is detected. In this embodiment this amount of needle detection is determined by monitoring the voltage from piezoelectric crystal 1006, this voltage being proportional to the amount of movement of the needle. The amount of power being fed to the needle is determined at step 1202. Step 1204 receives a voltage from the crystal 1002, and determines the amount of needle movement as a difference between a current voltage representing a current needle position and a previous voltage representing a previous needle position. At step 1206 the mechanical impedance presented to the needle is detected according to a proportionality between power detected in step 1202 and a amount of a needle movement detected at step 1204. The mechanical impedance may also be weighted by a weighting factor which may be a linear factor or may be itself dependent on power or movement amount. For instance, at higher powers the mechanical impedance may be a different ratio, since the material can only react by some maximum amount no matter how high the power. This mechanical impedance is then stored as a current value. At step 1208 a current resonant frequency is calculated based on the current amount of needle movement determined at step 1204. This may be done in many different ways, simplest among which might be to store a plurality of recent determined values and to conduct a fast Fourier transform on these values to determine current frequency components. The current mechanical impedance and current resonant frequency are then used to address the map to detect the part of the eye being operated on. In this preferred embodiment step 1210, which detects this part of the eye, outputs a number which is indicative of the part of the eye currently being operated on. For instance, number 1 might mean nucleus, 2 means lens and so on. Step 1212 then adjusts the power output, and aspiration and fluid control to follow the part of the eye operated on. The way in which the amount of power would be determined is similar to the way in which the map is determined—when using an actual model the values which cause punch-through and which are acceptable can be easily determined. Accordingly, this actual model can be used to determine what parameters output correspond to what degree of operation.

Of course it should be understood in the above flow chart that many modifications are possible. For example, while the flow chart explains that both mechanical impedance or resonant frequency be used, it should be understood that either one by itself may be enough to find the current location in the eye and hence a two dimensional map of either resonant frequency or mechanical impedance could be used. While the techniques of the present invention are specifically related to operation within a human eye, it should be emphasized that these techniques could be used for operation in many other organs or in anything else.

Figure 13:
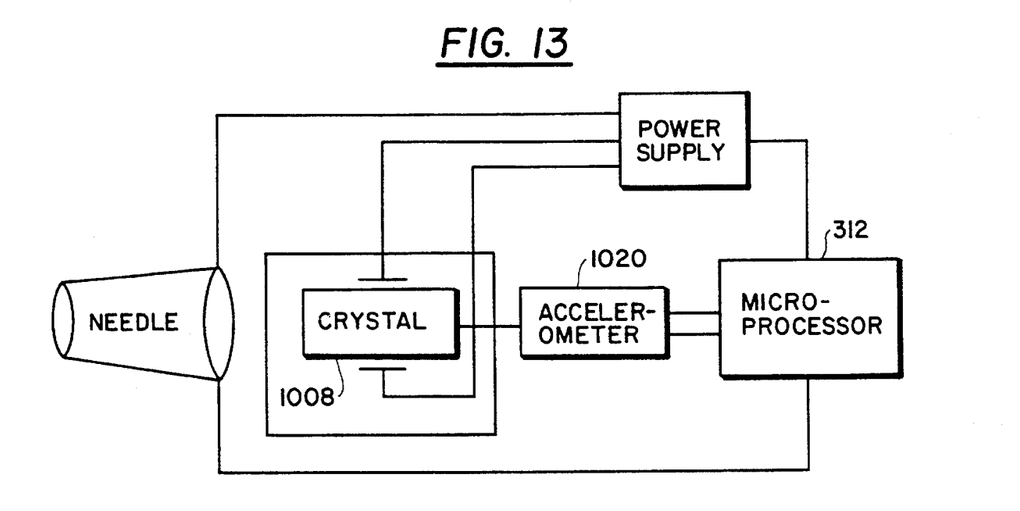
FIG. 13 shows a block diagram of a fifth embodiment of the invention.

FIG. 13 shows a fifth embodiment of the present invention which is an alternative to the fourth embodiment. This fifth embodiment uses at least one solid state accelerometer to detect the resonant frequency characteristic of the encountered needle load. FIG. 13 is simplified by removing all auxiliary structure used for the needle, and only shows the driving crystal 1008 and its mechanically linked accelerometer 1020. In this way, the microprocessor 312 receives information indicative of the amount of power driven to the crystal 1008 as well as the information from the accelerometer. An accelerometer is commonly available from many different sources. The fifth embodiment of FIG. 13 would operate similarly to that explained with reference to the flow chart of FIG. 12. In summary the accelerometer would be used to determine how rapidly the needle accelerates and decelerates and when a harder material is hit the structure would accelerate or decelerate slower under a heavier load, thereby providing an automated detection of material hardness. The force meter, in contrast, determines how much force the needle is encountering by how much it is moving. By the detection of how much force is on the needle, one can determine mechanical impedance.

Although only a few embodiments have been described in detail above, those having ordinary skill in the art will understand that many modifications are possible in this embodiment without detracting from the advantages of the invention. All such modifications are intended to be encompassed within the following application.

What is claimed:

1. A control system for a surgical transducer for operating on a human part, comprising:

means for monitoring mechanical impedance of the load to determine changes in characteristics of a load encountered by the surgical transducer; and means for controlling an operating characteristic of said transducer based on a relationship which is at least partly non-linear between said mechanical impedance and said operating characteristic.

2. A control system as in claim 1 wherein said controlling means includes means for weighting said mechanical impedance with a weighting factor which is dependent on an amount of driving of said transducer.

3. A control system as in claim 2 wherein said amount of driving of said transducer is a power of said transducer or a movement amount of said transducer.

4. A control system as in claim 1 wherein said controlling means comprises a processor which stores a map of said non-linear and linear relationship between mechanical impedance and said operating characteristics.

5. A control system for a surgical transducer for operating on a human part, comprising:

a monitoring device, which monitors mechanical impedance of a load, to determine changes in characteristics of the load encountered by the surgical transducer, said monitoring device including a solid state microsensor mechanically coupled to said surgical transducer to determine an amount of movement thereof and means for calculating mechanical impedance from said amount of movement and from electrical characteristics supplied to said transducer; and means for controlling an operating characteristic of said transducer based on said mechanical impedance.

6. A system as in claim 5, wherein said calculating means calculates said first characteristic by obtaining a quotient between voltage and current driving the surgical transducer.

7. A control system for a surgical transducer for operating on a human part, comprising:

a monitoring device, which monitors a first characteristic of a load, said first characteristic being one which is related to hardness of the load as a function of electrical characteristics to the surgical transducer to determine changes in characteristics of the load encountered by the surgical transducer, said monitoring device including a solid state microsensor coupled to said surgical transducer to determine an amount of movement thereof and means for calculating said first characteristic from said amount of movement and from a power supplied to said transducer; and means for controlling an operating characteristic of said transducer based on said first characteristic.

8. A system as in claim 7 wherein said solid state microsensor is a piezoelectric element mechanically coupled to said surgical transducer.

9. A system as in claim 7 wherein said microsensor is an accelerometer.

10. A method of controlling an operation in a human body part comprising the steps of:

forming a map between a mechanical impedance of different portions of said body part and a characteristic of a surgical instrument which will conduct the operation, said map indicating which characteristic should be used for said different mechanical impedances;

operating the surgical instrument to conduct said operation;

detecting a first mechanical impedance presented to the surgical instrument;

determining a relation between the first mechanical impedance presented to the surgical instrument with respect to a second mechanical impedance of a previous load presented to the surgical instrument;

automatically changing a function of the surgical instrument if said first mechanical impedance differs from said second mechanical impedance by a predetermined amount.

11. A method of controlling an operation in a human body part comprising the steps of:

forming a map between a mechanical impedance of different portions of said body part and a characteristic of a surgical instrument which will conduct the operation, said map indicating which characteristic should be used for said different portions, said map including a relationship between said characteristic and said mechanical impedance, which relationship is at least partially non-linear;

operating the surgical instrument to conduct said operation;

detecting a mechanical impedance presented to the surgical instrument;

determining a relation between the mechanical impedance presented to the surgical instrument with respect to a previous load presented to the surgical instrument;

automatically increasing an amount of driving if said mechanical impedance is greater than said previous load; and automatically decreasing said amount of driving if said mechanical impedance is less than said previous load.

12. A method as in claim 11 wherein said automatically increasing and said automatically decreasing steps drive a power of said transducer or a movement amount of said transducer.

13. An apparatus for enabling operations on a human body part comprising:

memory means for storing a map between mechanical impedance of said human body parts and a characteristic to be used in operation for that mechanical impedance;

a surgical tool, having a characteristic which can conduct the operation on said human body parts;

a mechanical sensor, coupled to said surgical tool for detecting properties of movement of said surgical tool; and processing means for detecting an amount of power provided to said surgical tool and calculating a mechanical impedance based on said properties of power and said amount of movement and for using said mechanical impedance to address said map to thereby obtain information indicative of said operation and to use said information to control said surgical tool.

14. A system as in claim 13 wherein said map also stores a resonant frequency of various portions of said body part and said processing means further includes means for calculating a current resonant frequency and means for using said resonant frequency along with said mechanical impedance to determine said characteristic.

15. A control system for a surgical transducer for operating on a human part, comprising:

first means for determining a relationship which is at least partially non-linear between characteristics of the human part and characteristics of the surgical transducer;

an impedance monitoring device, monitoring impedance of the human part to determine changes in characteristics of the human part encountered by the surgical transducer; and a processor, controlling an operating characteristic of said transducer based on said mechanical impedance and said at least partly non-linear relationship.

16. A system as in claim 15 wherein said first means is a memory storing a map.

17. A system as in claim 15 wherein said operating characteristic includes a characteristic from the group consisting of aspiration control or power supply control.

18. A system as in claim 15 wherein said operating characteristic is frequency of the transducer.

19. A method of controlling a surgical transducer operating on a human part, comprising:

determining a relationship which is at least partly non-linear between characteristics of the human part and characteristics of the surgical transducer;

monitoring mechanical impedance of the human part to determine changes in characteristics of the human part encountered by the surgical transducer; and controlling an operating characteristic of said transducer based on said mechanical impedance and said at least partly non-linear relationship.

20. A method as in claim 19 wherein said controlling an operating characteristic controls a characteristic from the group consisting of aspiration control or power supply control.

21. A method as in claim 19 wherein said controlling an operating characteristic controls frequency of the transducer.

22. A method of controlling a surgical transducer, comprising the steps of:
   determining, for a particular transducer, the linearity relationship between hardness of a material encountered by the transducer and resonant frequency;
   monitoring a characteristic of the transducer during an operation on a load;
   adjusting said transducer using said determined nonlinear relationship, to produce an adjusted characteristic;
   controlling the operation of said transducer using said adjusted characteristic.

23. A method as in claim 22 wherein said controlling operation of said transducer includes controlling driving power to the transducer or controlling aspiration.

24. A method as in claim 22 wherein said monitoring a characteristic step determines said hardness from mechanical impedance, and said determining step is a step of determining a relationship between mechanical impedance and resonant frequency.

25. A method as in claim 22 wherein said monitoring a characteristic comprises determining frequency.

26. A control system for a surgical transducer for operating on a human part, comprising:
   a monitoring device, which monitors mechanical impedance of a load, to determine changes in characteristics of the load encountered by the surgical transducer, which characteristics affect an amount of reaction of said surgical transducer for a particular driving amount; and
   means for controlling an operating characteristic of said transducer which changes said amount of reaction, based on said mechanical impedance.

27. A method of controlling an operation in a human body part comprising the steps of:
   determining a relation which is at least partially non-linear between mechanical impedance of different materials and a characteristic of a surgical instrument which will conduct the operation, said relation indicating an amount of a characteristic which should be used for said different mechanical impedances;
   operating the surgical instrument to conduct said operation according to said amount of said characteristic;
   detecting a first impedance presented to the surgical instrument;
   tracking said first impedance relative to a second impedance of a previous load presented to the surgical instrument;
   automatically changing the characteristic of the surgical instrument according to said tracking and said relation.

28. An apparatus for enabling operations on a human body part comprising:
   memory means for storing a relation between mechanical impedance of said human body parts and a characteristic to be used in operation for that mechanical impedance;
   a surgical tool, having a characteristic which can conduct the operation on said human body parts;
   a sensor, coupled to said surgical tool for detecting properties of movement of said surgical tool; and
   processing means for detecting electrical characteristics provided to said surgical tool and determining a mechanical impedance based on said amount of electrical characteristics and said properties of movement and for using said mechanical impedance and said relation to obtain information indicative of said operation and to use said information to control said surgical tool.

29. A system as in claim 28 wherein said relation also indicates a resonant frequency of various portions of said body part and said processing means further includes means for calculating a current resonant frequency and means for using said resonant frequency along with said mechanical impedance to determine said characteristic.

* * * * *